United States Patent
Burk et al.

(10) Patent No.: US 8,609,658 B2
(45) Date of Patent: Dec. 17, 2013

(54) N,N-DIALKYLALKYLENYL ESTERS, COMPOSITIONS THEREOF, AND METHODS FOR USE THEREOF

(75) Inventors: Robert M. Burk, Laguna Beach, CA (US); David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/558,007

(22) Filed: Jul. 25, 2012

(65) Prior Publication Data

US 2013/0029992 A1 Jan. 31, 2013

Related U.S. Application Data

(60) Provisional application No. 61/152,119, filed on Jul. 27, 2011.

(51) Int. Cl.
| | | |
|---|---|---|
| *C07C 233/87* | (2006.01) | |
| *C07C 233/75* | (2006.01) | |
| *A61K 31/535* | (2006.01) | |

(52) U.S. Cl.
USPC ........................................ 514/239.5; 514/913

(58) Field of Classification Search
None
See application file for complete search history.

(56) References Cited

U.S. PATENT DOCUMENTS

| | | |
|---|---|---|
| 4,166,452 A | 9/1979 | Generales |
| 4,256,108 A | 3/1981 | Theeuwes |
| 4,265,874 A | 5/1981 | Bonsen |

FOREIGN PATENT DOCUMENTS

WO  WO 2009098458 A2 * 8/2009

OTHER PUBLICATIONS

Remington's Pharmaceutical Sciences, 16th Edition, 1980.

* cited by examiner

*Primary Examiner* — Jason M Sims
*Assistant Examiner* — Tori M Strong
(74) *Attorney, Agent, or Firm* — Krishna G. Banerjee; Debra D. Condino

(57) ABSTRACT

The invention provides well defined N,N-dialkylalkenyl ester compounds for treating glaucoma or ocular hypertension. The esters of the invention are particularly advantageous due to their stability in aqueous solutions.

17 Claims, No Drawings

N,N-DIALKYLALKYLENYL ESTERS, COMPOSITIONS THEREOF, AND METHODS FOR USE THEREOF

CROSS-REFERENCE TO RELATED APPLICATION

This application claims benefit to U.S. provisional application Ser. No. 61/512,119, filed Jul. 27, 2011, which is hereby incorporated by reference in its entirety.

FIELD OF THE INVENTION

The invention relates generally to compounds and methods for the treatment of ocular disorders, and more particularly to the use of well defined N,N-dialkylalkenyl ester compounds for the treatment of glaucoma and ocular hypertension.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

SUMMARY OF THE INVENTION

The invention provides well defined N,N-dialkylalkenyl ester compounds for treating glaucoma or ocular hypertension. The esters of the invention are particularly advantageous due to their stability in aqueous solutions. As such, the compounds of the invention can be readily incorporated into stable aqueous formulations useful for treating certain ocular conditions. In one embodiment of the invention, there are provided compounds having the structure

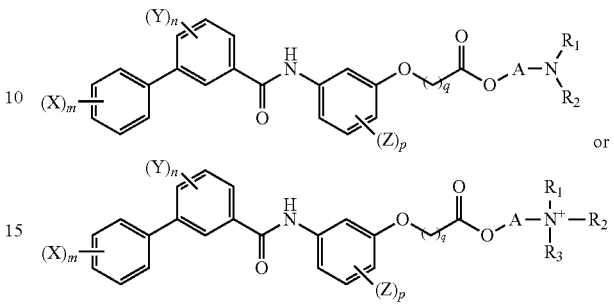

wherein:
each X, Y, and Z is independently selected from alkyl, alkoxy, or halogen;
A is optionally substituted alkylene or optionally substituted arylene;
$R_1$, $R_2$, and $R_3$ are each independently selected from H or $C_1$ to $C_6$ alkyl; or $R_1$ and $R_2$ are taken together to form a heterocyclic moiety;
m is 0 to 5;
n and p are each independently 0 to 4; and
q is 1-6.

In another embodiment of the invention, there are provided pharmaceutical compositions including at least one compound of the invention, the compound being present alone or in combination with one or more pharmaceutically acceptable excipients.

In another embodiment of the invention, there are provided compositions including at least one compound of the invention, wherein the composition is a liquid which is ophthalmically acceptable.

In a further embodiment of the invention there are provided methods for the treatment of glaucoma or ocular hypertension. Such methods can be performed, for example, by administering to a subject in need thereof a therapeutically effective amount of at least one compound of the invention.

In a further embodiment of the invention there are provided methods for reducing intraocular pressure. Such methods can be performed for example, by administering to a subject in need thereof a therapeutically effective amount of at least one compound of the invention.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —$CH_2O R_7$, —C(O)—, —C(O)—, —S—, —$S(O)_2$, —OC(O)—O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkylene" refers to a divalent alkyl moiety. In other words, an "alkylene" moiety has two pints of attachment to the rest of the molecule.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein "arylene" refers to an aryl ring or ring system or a heteroaryl ring or ring system which connects two other parts of a molecule, i.e. the two parts are bonded to the ring in two distinct ring positions. Arylene or heteroarylene may be substituted or unsubstituted. Unsubstituted arylene or heteroarylene has no substituents other than the two parts of the molecule it connects. Substituted arylene or heteroarylene has substituents in addition to the two parts of the molecule it connects.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

The invention provides well defined N,N-dialkylalkenyl ester compounds for treating glaucoma or ocular hypertension. The esters of the invention are particularly advantageous due to the increased stability in aqueous solution relative to the corresponding carboxylic acids. The esters of the invention may be considered "prodrugs" of the corresponding carboxylic acids. "Prodrug" refers to a compound which converts to a therapeutically active compound after administration and is used herein as it is generally understood in the art. Conversion of the prodrug into an activated form may occur by hydrolysis of an ester group or some other biologically labile group. Generally, but not necessarily, a prodrug is inactive or less active than the therapeutically active compound into which it is converted.

In one embodiment of the invention, there are provided compounds having the structure

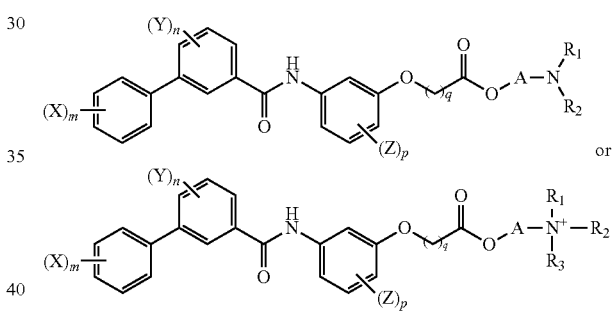

wherein:
each X, Y, and Z is independently selected from alkyl, alkoxy, or halogen;
A is optionally substituted alkylene or optionally substituted arylene;
$R_1$, $R_2$, and $R_3$ are each independently selected from H or $C_1$ to $C_6$ alkyl; or $R_1$ and $R_2$ are taken together to form a heterocyclic moiety;
m is 0 to 5;
n and p are each independently 0 to 4; and
q is 1-6.

In some embodiments of the invention, A is alkylene. In some embodiments, A is $C_1$ to $C_6$ alkylene. In certain embodiments, A is $C_3$ alkylene.

In other embodiments of the invention A is arylene. In some embodiments A is phenylene.

In some embodiments of the invention X is halogen. In some embodiments, X is fluoride.

In certain embodiments of the invention, $R_1$, $R_2$, and $R_3$ are each independently $C_1$ to $C_3$ alkyl. In some embodiments, $R_1$ and $R_2$ are taken together to form a morpholino moiety.

Exemplary compounds contemplated for use in the practice of the invention include, but are not limited to, compounds having any one of the structures:

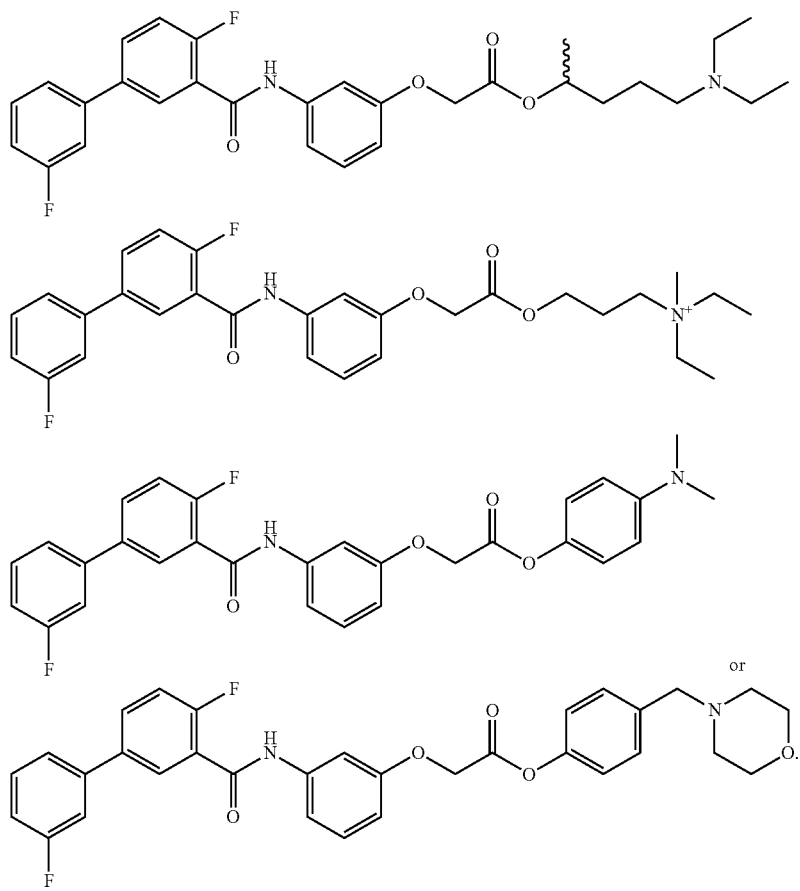

In some embodiments of the invention, the compound has the structure

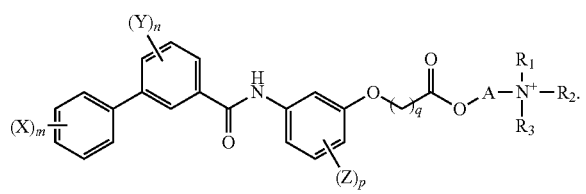

Thus, in the practice of the invention, the cations set forth above may form a pharmaceutically acceptable salt with pharmaceutically acceptable anions, such as for example, the hydrochloride, hydrobromide, hydroiodide, sulfate, bisulfate, phosphate or acid phosphate, acetate, maleate, fumarate, oxalate, lactate, tartrate, citrate, gluconate, saccharate, p-toluenesulfonate salts, and the like. A pharmaceutically acceptable salt may be any salt which retains the activity of the parent compound and does not impart any deleterious or untoward effect on the subject to which it is administered and by the context in which it is administered.

The invention also relates to pharmaceutical compositions including at least one compound of the invention, the compound being alone or in combination with one or more pharmaceutically acceptable excipients. The invention also relates to methods for the treatment of glaucoma or ocular hypertension. Such methods can be performed, for example, by administering to a subject in need thereof an ophthalmically acceptable pharmaceutical composition containing a therapeutically effective amount of at least one compound of the invention.

An ophthalmically acceptable pharmaceutical composition is one that can be administered topically to the eye of a subject in need thereof. Comfort to the subject being administered the composition should be maximized, but other considerations, such as drug stability, may necessitate a pharmaceutical composition that provides less than optimal comfort. In such a case, the composition should be formulated such that it is tolerable to a subject being administered the composition topically.

The pharmaceutical composition can be administered topically in the form of solutions or suspensions, ointments, gels, creams, etc. A "pharmaceutically acceptable excipient" is one that is compatible with the active ingredient of the composition and not harmful to the subject being administered the pharmaceutical composition. Solutions for ophthalmic application are often prepared using physiological saline as a major vehicle. Other vehicles include polyvinyl alcohol, povidone, hydroxypropyl methyl cellulose, poloxamers, carboxymethyl cellulose, hydroxyethyl cellulose, and purified water. Examples of useful excipients also include preservatives, buffers, other pH adjustors, tonicity adjustors, surfactants, antioxidants, and chelating agents.

Useful preservatives include benzalkonium chloride, chlorobutanol, thimerosal, phenylmercuric acetate and phenylmercuric nitrate. Examples of buffers include phosphate, borate, sulfate, acetate, and citrate buffers. Acids or bases may be used to adjust the pH of the compositions as needed.

Examples of tonicity agents include glycerin, mannitol, sodium chloride and potassium chloride. Useful surfactants include, for example, Tween 80. Examples of ophthalmically acceptable antioxidants include sodium metabisulfite, sodium thiosulfate, acetylcysteine, butylated hydroxyanisole and butylated hydroxytoluene. A useful chelating agent is edentate disodium.

Mixtures of two or more of any suitable excipients may be used. The aforementioned examples are not intended to limit the scope of the invention in any way.

The ingredients are usually used in the following amounts:

| Ingredient | Amount (Weight/Volume Percentage) |
|---|---|
| active ingredient | About 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

A therapeutically effective amount of at least one compound of the invention in the pharmaceutical composition disclosed herein is an amount useful to observe a therapeutic effect as compared to a placebo composition that, except for the absence of a compound of the invention, is otherwise identical to the pharmaceutical composition. The amount of at least one compound of the invention to administer depends on factors such as the intended therapeutic effects, the specific mammal in need thereof, the severity and nature of the mammal's condition, the manner of administration, the potency and pharmacodynamics of the particular compound, and the judgment of the prescribing physician. The therapeutically effective dosage of at least one compound of the invention is preferably in the range of about 0.5 or about 1 to about 100 mg/kg/day.

Also, an ophthalmically acceptable pharmaceutical composition should be packaged for single use, or contain a preservative to prevent contamination over multiple uses.

Aside from topical application to treat diseases affecting the eye including glaucoma, pharmaceutical compositions containing at least one compound of the invention can also be administered periocularly, intraocularly, or by other effective means available in the art.

Persons skilled in the art would readily understand that a drug containing one or more of the compounds disclosed herein can be confected as a powder, pill, tablet or the like, or as a solution, emulsion, suspension, aerosol, syrup or elixir suitable for oral or parenteral administration or inhalation. For solid dosage forms or medicaments, non-toxic solid excipients for admixture with compounds disclosed herein include, but are not limited to, pharmaceutical grades of mannitol, lactose, starch, magnesium stearate, sodium saccharin, polyalkylene glycols, talcum, cellulose, glucose, sucrose, and magnesium carbonate. The solid dosage forms may be coated by a material such as glyceryl monostearate or glyceryl distearate, which is utilized in known techniques to delay disintegration and absorption in the gastrointestinal tract for the purpose of providing a sustained action over a longer period. Solid dosage forms may also be coated by the techniques described in U.S. Pat. Nos. 4,256,108, 4,166,452 and 4,265,874 to form osmotic therapeutic tablets for control release.

Pharmaceutically administrable liquid dosage forms can, for example, comprise a solution or suspension of at least one of the compounds disclosed herein and optional pharmaceutical adjutants in a carrier, such as water, saline, aqueous dextrose, glycerol, ethanol and the like. The liquid dosage forms may also contain nontoxic auxiliary substances such as wetting or emulsifying agents, pH buffering agents and the like. Examples of such auxiliary agents include sodium acetate, sorbitan monolaurate, triethanolamine, sodium acetate, triethanolamine oleate, etc. Methods for preparing such dosage forms are well-known to persons skilled in the art (see, for example, Remington's Pharmaceutical Sciences, Mack Publishing Company, Easton, Pa., 16$^{th}$ Edition, 1980).

Parenteral administration is generally characterized by subcutaneous, intramuscular, or intravenous injection. Injectables can be prepared as liquid solutions or suspensions, solid forms that can be reconstituted into solutions or suspensions prior to injection, or as emulsions. Suitable excipients include water, saline dextrose, glycerol, ethanol and the like. Such injectable pharmaceutical compositions may also contain minor amounts of non-toxic auxiliary substances such as wetting or emulsifying agents, pH buffers and the like. Examples mentioned herein are not intended to limit the scope of the invention in any way.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

The following examples are intended only to illustrate the invention and should in no way be construed as limiting the invention.

EXAMPLES

TABLE 1

| Formulation Vehicle Compositions | |
|---|---|
| Ingredients (% w/w) | |
| Invention Compound | 0.0005% w/w (5 ppm) |
| Sodium Phosphate Dibasic Heptahydrate | 0.34 |
| Citric acid Monohydrate | 0.072 |
| Sodium Chloride | 0.82 |
| Polysorbate 80 (super refine) | 0.5 |
| NaOH/HCL (1N) | Adjust to pH 6 |
| Purified water | q s |

| Compound | % Substrate Remaining | | |
|---|---|---|---|
| | 7 days/25° C. | 28 days/25° C. | 7 days/40° C. |
| [structure] | 101.2 | 94.4 | 92 |
| [structure] | 95.5 | 82.6 | 49.2 |
| [structure] | 92 | 78 | 78.8 |
| [structure] | 61.5 | 12 | 18 |

As can be seen from the data above, the compounds of the invention exhibit substantial aqueous stability, thereby allowing these compounds to be formulated as aqueous solutions for the treatment of certain pathological ocular conditions.

While this invention has been described with respect to these specific examples, it is understood that other modifications and variations are possible without departing from the spirit of the invention.

What is claimed is:

1. A compound of the structure:

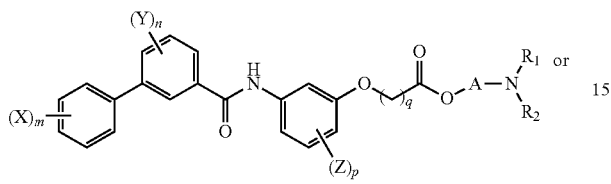

or

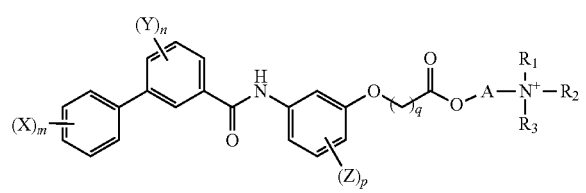

wherein:
each X, Y, and Z are independently selected from alkyl, alkoxy, or halogen;
A is optionally substituted alkylene or optionally substituted arylene;
$R_1$, $R_2$, and $R_3$ are each independently selected from H or $C_1$ to $C_6$ alkyl; or $R_1$ and $R_2$ are taken together to form a heterocyclic moiety;
m is 0 to 5;
n and p are each independently 0 to 4; and
q is 1-6.

2. The compound of claim 1 wherein A is alkylene.
3. The compound of claim 1 wherein A is $C_1$ to $C_6$ alkylene.
4. The compound of claim 1 wherein A is $C_3$ alkylene.
5. The compound of claim 1 wherein A is arylene.
6. The compound of claim 1 wherein A is phenylene.
7. The compound of claim 1 wherein X is halogen.
8. The compound of claim 1 wherein X is fluoride.
9. The compound of claim 1 wherein $R_1$, $R_2$, and $R_3$ are each independently $C_1$ to $C_3$ alkyl.
10. The compound of claim 1 wherein $R_1$ and $R_2$ are taken together to form a morpholino moiety.
11. The compound of claim 1 having any one of the structures:

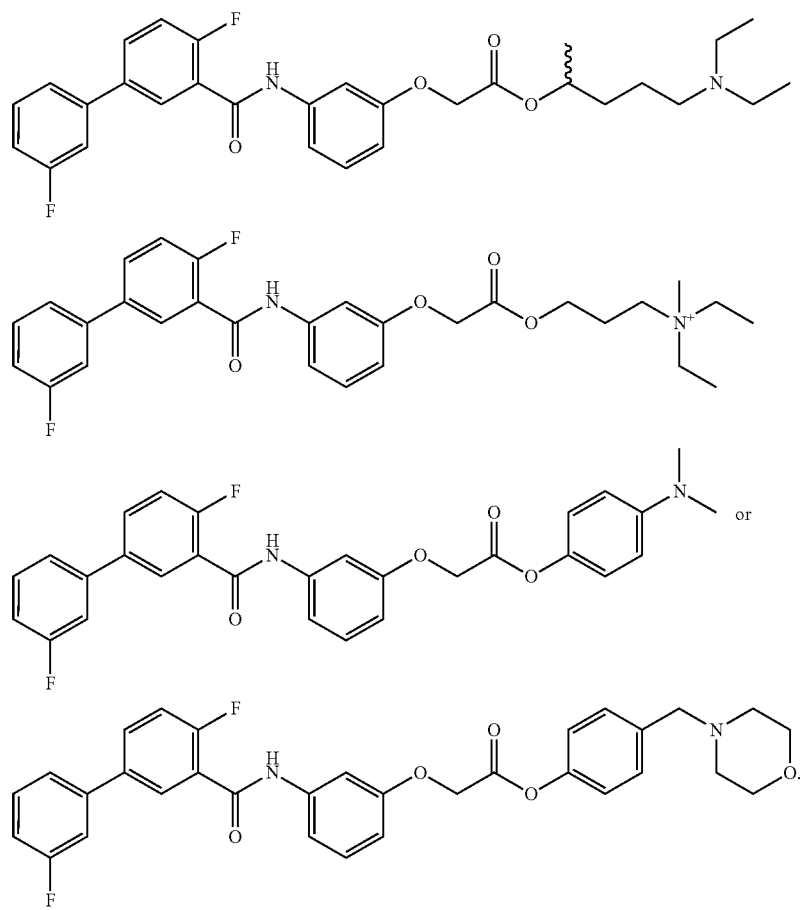

12. A pharmaceutical composition comprising at least one compound of claim 1, the compound being present alone or in combination with one or more pharmaceutically acceptable excipients.

13. A composition comprising at least one compound according to claim 1, wherein the composition is a liquid which is ophthalmically acceptable.

14. A method for the treatment of glaucoma or ocular hypertension comprising administering to a subject in need thereof a therapeutically effective amount of at least one compound to claim 1.

15. The method of claim 14 wherein the subject is human.

16. A method of reducing intraocular pressure comprising administering to a subject in need thereof a therapeutically effective amount of at least one compound of claim 1.

17. The method of claim 16 wherein the subject is human.

* * * * *